US012612349B2

(12) United States Patent
Sainani et al.

(10) Patent No.: US 12,612,349 B2
(45) Date of Patent: Apr. 28, 2026

(54) PROCESS FOR THE PREPARATION OF 2-ISOPENTYL-2-ISOPROPYL-1,3-DIMETHOXYPROPANE

(71) Applicant: SABIC GLOBAL TECHNOLOGIES B.V., Bergen Op Zoom (NL)

(72) Inventors: Jaiprakash Brijlal Sainani, Vadodara (IN); Kiran Arunkumar Puthamane, Bangalore (IN); Shirish Shrikant Abhyankar, Bangalore (IN); Omkar Gadgil, Pen (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 463 days.

(21) Appl. No.: 18/031,506

(22) PCT Filed: Oct. 13, 2020

(86) PCT No.: PCT/EP2020/078730
§ 371 (c)(1),
(2) Date: Apr. 12, 2023

(87) PCT Pub. No.: WO2022/078576
PCT Pub. Date: Apr. 21, 2022

(65) Prior Publication Data

US 2023/0373891 A1 Nov. 23, 2023

(51) Int. Cl.

| | |
|---|---|
| ***C07C 41/16*** | (2006.01) |
| ***C07C 29/38*** | (2006.01) |
| ***C07C 41/34*** | (2006.01) |
| ***C07C 41/42*** | (2006.01) |
| ***C07C 45/62*** | (2006.01) |
| ***C07C 45/74*** | (2006.01) |

(52) U.S. Cl.
CPC .............. *C07C 41/16* (2013.01); *C07C 29/38* (2013.01); *C07C 41/34* (2013.01); *C07C 41/42* (2013.01); *C07C 45/62* (2013.01); *C07C 45/74* (2013.01)

(58) Field of Classification Search
CPC ......... C07C 41/16; C07C 41/34; C07C 41/42; C07C 29/38; C07C 45/62; C07C 45/74
See application file for complete search history.

(56) References Cited

U.S. PATENT DOCUMENTS 5,371,299 A * 12/1994 Borsotti .................. C07C 43/10 568/660
2013/0253132 A1 9/2013 Mijolovic et al.

FOREIGN PATENT DOCUMENTS

| | | | |
|---|---|---|---|
| CN | 102432439 | A | 5/2012 |
| EP | 0361493 | A1 | 4/1990 |
| EP | 0487035 | A2 | 5/1992 |
| JP | 115760 | A | 1/1990 |

OTHER PUBLICATIONS

International Search Report for International Application No. PCT/EP2020/078730, International Filing Date Oct. 13, 2020, Date of Mailing Jul. 8, 2021, 4 pages.
Written Opinion for International Application No. PCT/EP2020/078730, International Filing Date Oct. 13, 2020, Date of Mailing Jul. 8, 2021, 6 pages.

* cited by examiner

*Primary Examiner* — Medhanit W Bahta
(74) *Attorney, Agent, or Firm* — CANTOR COLBURN LLP

(57) ABSTRACT

The present invention relates to a process for the preparation of 2-isopentyl-2- isopropyl-1,3-dimethoxypropane, said process comprising the steps of: i) contacting iso-valeraldehyde with an aqueous solution of a hydroxide base selected from the group consisting of sodium hydroxide (NaOH), potassium hydroxide (KOH) or a combination thereof, said solution having an amount of said hydroxide base of at least 20% w/v, and (m) ethanol; form (2Z)-2-isopropyl-5-methyl-2-hexenal; step ii) contacting (2Z)-2-iso-propyl-5-methyl-2-hexenal with a reducing system to form 2-isopropyl-5-methylhexanal; step iii) contacting 2-isopropyl-5-methylhexanal with formaldehyde and an inorganic base to form 2-isopentyl-2-isopropylpropane-1,3-diol; and step iv) contacting 2-isopentyl-2-isopropylpropane-1,3-diol with a methylation agent and a base to form 2-isopentyl-2-isopropyl-1,3-dimethoxypropane.

9 Claims, No Drawings

PROCESS FOR THE PREPARATION OF 2-ISOPENTYL-2-ISOPROPYL-1,3-DIMETHOXY-PROPANE

CROSS REFERENCE TO RELATED APPLICATIONS

This application is a National Stage application of PCT/EP2020/078730, filed Oct. 13, 2020, which is incorporated by reference in its entirety herein.

BACKGROUND

Several methods have been reported in literature for the preparation of diethers compounds, especially 2,2-disubstituted-1,3-dimethoxy propane, such as 2-isopentyl-2-isopropyl-1,3-dimethoxypropane.

EP 0 361 493 A1 discloses the alkylation of diethyl malonate using ethyl malonate, alkyl bromide and lithium aluminium hydride which are costly and not necessarily environmentally benign.

EP 0 487 035 A2 discloses a process for the preparation of 2-isopentyl2-isopropyl-1,3-dimethoxypropane from iso-valeraldehyde in four steps. In the first step, an aldol condensation is carried out in the presence of an ion-exchange resin with an extremely basic function, for instance quaternary ammonium hydroxide in order to limit the formation of polycondensate.

CN102432439A discloses a process for the preparation of 2-isopentyl2-isopropyl-1,3-dimethoxypropane from iso-valeraldehyde (1.3-methyl-butyraldehyde) in a pressurized aqueous solution of 1-10% NaOH aqueous solution as catalyst to perform an aldol condensation reaction, which is then reduced using a Pd/C catalyst in presence of H2, followed by formulation in inorganic alkali and finally methylation using a base and $CH_3Cl$.

JP11-005760 discloses a method of methylation of a diol to a diether by using NaH and MeCl in an aprotic solvent, such as DMF or acetonitrile.

SUMMARY

It is an object of the present invention to provide an improved and alternate method for the synthesis of 2-isopentyl-2-isopropyl-1,3-dimethoxypropane that is industrially viable, sustainable and economical. It is a further object of the present invention to provide a method with reduced costs and safer reagents than prior art methods.

The present invention relates to a process for the preparation of a 2,2-disubstituted 1,3-diether compound, specifically to a process for the preparation of 2-isopentyl-2-isopropyl-1,3-dimethoxypropane (Formula 1) as shown in the graph below.

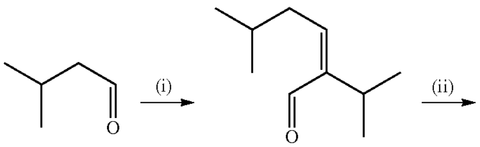

Formula-A

Formula-B

-continued

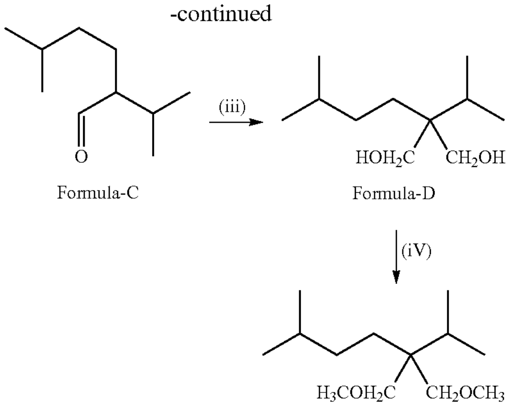

Formula-C

Formula-D

Formula-1

The process of the invention comprising four subsequent steps, viz. step i), step ii), step iii) and step iv).

The first step, step i), entails contacting iso-valeraldehyde (also known as 3-methylbutanal) according to Formula A with an aqueous solution of a hydroxide base selected from the group consisting of sodium hydroxide (NaOH), potassium hydroxide (KOH) or a combination thereof, said solution having an amount of said hydroxide base of at least 15% w/v, preferably at least 20% w/v, and (m) ethanol; to form (2Z)-2-isopropyl-5-methyl-2-hexenal (Formula B). The present inventors have found that the combination of a strong hydroxide solution and methanol provides excellent results with low formation of polycondensates without the need for special equipment or chemicals. The inventors have observed, without wishing to be bound by a particular theory, that methanol (and/or ethanol) helps in getting the reaction started at a relatively low temperature (e.g. between 30 and 50° C.). Ethanol may also be used instead of methanol.

Preferentially, the molar ratio between (m)ethanol and the hydroxide is between 4.0:1.0 and 8.0:1.0, such as between 5.0:1.0 and 7.0:1:0, there may be approx. 6 times as much mole of (m)ethanol as hydroxide.

The second step is step ii) contacting (2Z)-2-isopropyl-5-methyl-2-hexenal according to Formula B with a reducing catalyst system to form 2-isopropyl-5-methylhexanal according to Formula C.

The third step is step iii) contacting 2-isopropyl-5-methylhexanal according to Formula C with formaldehyde and an inorganic base to form 2-isopentyl-2-isopropylpropane-1,3-diol (also known as 2-isopentyl-2-(3-methylbutyl)-1,3-propanediol) according to Formula D.

The fourth step is step iv) contacting 2-isopentyl-2-isopropylpropane-1,3-diol (Formula D) with a methylation agent and a base to form 2-isopentyl-2-isopropyl-1,3-dimethoxypropane (Formula 1).

DEFINITIONS

The following definitions are used in the present description and claims to define the stated subject matter. Other terms not cited below are meant to have the generally accepted meaning in the field.

- "halide" as used in the present description means: an ion selected from the group of: fluoride (F—), chloride (Cl—), bromide (Br—) or iodide (I—).
- "(m)ethanol as used in the present description means: methanol and/or ethanol, in other words methanol or ethanol or a combination thereof.

"room temperature" as used in the present invention means a temperature of 23° C.

"ambient pressure" as used in the present invention means atmospheric pressure (atm), being 1013.25 mbar (101325 Pa).

The present invention is described below in more detail. All embodiments described with respect to one aspect of the present invention are also applicable to the other aspects of the invention, unless otherwise stated.

DETAILED DESCRIPTION

The present invention relates to a process for the preparation of 2-isopentyl-2-isopropyl-1,3-dimethoxypropane (Formula 1), said process comprising the steps of: i) contacting iso-valeraldehyde (Formula A) with an aqueous solution of a hydroxide base selected from the group consisting of sodium hydroxide (NaOH), potassium hydroxide (KOH) or a combination thereof, said solution having an amount of said hydroxide base of at least 15% w/v, and methanol (or ethanol); to form (2Z)-2-isopropyl-5-methyl-2-hexenal (Formula B); ii) contacting (2Z)-2-isopropyl-5-methyl2-hexenal (Formula B) with a reducing catalyst system to form 2-isopropyl-5-methylhexanal (Formula C); iii) contacting 2-isopropyl-5-methylhexanal (Formula C) with formaldehyde and an inorganic base to form 2-isopentyl-2-isopropylpropane-1,3-diol (Formula D); and iv) contacting 2-isopentyl-2-isopropylpropane-1,3-diol (Formula D) with a methylation agent and a base to form 2-isopentyl-2-isopropyl-1,3-dimethoxypropane (Formula 1).

In an embodiment, step i) comprises:

contacting iso-valeraldehyde (Formula A) with methanol and gradually adding the aqueous solution of a hydroxide base, preferably over a period of between 20 and 50 minutes, while the temperature is maintained below 45° C.;

after completion of the addition of the hydroxide heating the reaction mixture to a temperature of between 45 and 60° C. and maintained at that temperature for a period of between 10 and 50 minutes;

separating an aqueous hydroxide phase from an organic product phase;

optionally washing the organic product phase with water to obtain the product as an oil.

In an embodiment, step ii) comprises:

contacting (2Z)-2-isopropyl-5-methyl-2-hexenal (Formula B) with an aqueous solution of hydroxide;

adding Ni/Al alloy in at least three portions, each portion being added gradually over a period of between 30 and 60 minutes and stirring the reaction mixture in between the addition of each portion for a period of between 30 and 60 minutes; while maintaining the temperature between 15 and 25° C.

removing the alloy by filtration; optionally washing the rententate with water;

separating an aqueous hydroxide phase of the filtrate from an organic product phase;

optionally extracting the aqueous hydroxide phase with an organic extractant which extract is combined with the organic product phase;

evaporating the organic product phase to obtain the product according to Formula C.

In an embodiment, step iii) comprises:

contacting 2-isopropyl-5-methylhexanal (Formula C) with formaldehyde and methanol;

gradually adding an inorganic base, preferably over a period of between 40 and 80 minutes, while the temperature is kept below 45° C.;

after completion of the addition of the base heating the reaction mixture to a temperature of between 45 and 60° C. and maintained at that temperature for a period of between 30 and 60 minutes;

separating an aqueous hydroxide phase from an organic product phase;

optionally extracting the aqueous hydroxide phase with an organic extractant which extract is combined with the organic product phase;

evaporating the organic product phase to obtain crude 2-isopentyl-2-isopropylpropane-1,3-diol (Formula D);

optionally purifying the product obtained by (vacuum) distillation.

In an embodiment, step iv) comprises:

contacting 2-isopentyl-2-isopropylpropane-1,3-diol (Formula D) with one or more solvents;

gradually adding a base;

after completing of the addition allowing the reaction mixture to react for a period of between 10 and 50 minutes;

adding methyl iodide in at least two portions, and stirring the reaction mixture in between the addition of each portion for a period of between 10 and 50 minutes; preferably while maintaining the temperature below 30° C.

after completing of the addition allowing the reaction mixture to react for a period of between 8 and 14 hours, preferably between 10 and 12 hours;

separating an aqueous hydroxide phase from an organic product phase being crude 2-isopentyl-2-isopropyl-1,3-dimethoxypropane;

optionally washing the crude 2-isopentyl-2-isopropyl-1,3-dimethoxypropane with water to obtain 2-isopentyl-2-isopropyl-1,3-dimethoxypropane as an oil.

In a specific embodiment, each of the four specific embodiments disclosed above—each specifying a process step i), ii), iii) and iv)—are combined. This leads to the following specific embodiment for the process.

Process comprising the following steps:

contacting iso-valeraldehyde (Formula A) with methanol and gradually adding the aqueous solution of a hydroxide base, preferably over a period of between 20 and 50 minutes, while the temperature is maintained below 45° C.;

after completion of the addition of the hydroxide heating the reaction mixture to a temperature of between 45 and 60° C. and maintained at that temperature for a period of between 10 and 50 minutes;

separating an aqueous hydroxide phase from an organic product phase; * optionally washing the organic product phase with water to obtain (2Z)-2-isopropyl-5-methyl-2-hexenal (Formula B) as an oil;

contacting (2Z)-2-isopropyl-5-methyl-2-hexenal (Formula B) with an aqueous solution of hydroxide;

adding Ni/Al alloy in at least three portions, each portion being added gradually over a period of between 30 and 60 minutes and stirring the reaction mixture in between the addition of each portion for a period of between 30 and 60 minutes; while maintaining the temperature between 15 and 25° C.;

removing the alloy by filtration; optionally washing the rententate with water;

separating an aqueous hydroxide phase of the filtrate from an organic product phase;

optionally extracting the aqueous hydroxide phase with an organic extractant which extract is combined with the organic product phase;

evaporating the organic product phase to obtain 2-isopropyl-5-methylhexanal according to Formula C;

contacting 2-isopropyl-5-methylhexanal (Formula C) with formaldehyde and methanol;

gradually adding an inorganic base, preferably over a period of between 40 and 80 minutes, while the temperature is kept below 45° C.;

after completion of the addition of the base heating the reaction mixture to a temperature of between 45 and 60° C. and maintained at that temperature for a period of between 30 and 60 minutes;

separating an aqueous hydroxide phase from an organic product phase;

optionally extracting the aqueous hydroxide phase with an organic extractant which extract is combined with the organic product phase;

evaporating the organic product phase to obtain crude 2-isopentyl-2-isopropylpropane-1,3-diol (Formula D);

optionally purifying the product obtained by (vacuum) distillation to obtain 2-isopentyl-2-isopropylpropane-1,3-diol (Formula D);

contacting 2-isopentyl-2-isopropylpropane-1,3-diol (Formula D) with one or more solvents;

gradually adding a base;

after completing of the addition allowing the reaction mixture to react for a period of between 10 and 50 minutes;

adding methyl iodide in at least two portions, and stirring the reaction mixture in between the addition of each portion for a period of between 10 and 50 minutes; preferably while maintaining the temperature below 30° C.;

after completing of the addition allowing the reaction mixture to react for a period of between 8 and 14 hours, preferably between 10 and 12 hours;

separating an aqueous hydroxide phase from an organic product phase;

optionally washing the organic product phase with water to obtain 2-isopentyl-2-isopropyl-1,3-dimethoxypropane (Formula 1) as an oil.

Each of the four steps is described in more detail below.

First Step, Step i)—Aldol Condensation

The present inventors have observed that with the novel method of aldol condensation using a mixture of an aqueous solution of a hydroxide base (strength of at least 15% w/v, preferably at least 20% w/v) and (m)ethanol excellent conversion is obtained without a large amount of polycondensate by-products being formed. Prior art processes use lower strength hydroxide base solutions and/or do not use (m)ethanol these have shown to only provide good yields under conditions of pressure and/or long duration and/or high temperature.

With the method according to the present invention it is possible to carry out the method at room temperature at ambient pressure. The presence of either methanol or ethanol (or both) has a beneficial effect on reducing the amount of by-products. This is clear from the experimental part below. Without wishing to be bound by a particular theory, the present inventors believe that (m)ethanol aids in keeping any by-products formed in the aqueous phase, whereas the product is extracted in the organic phase. Moreover, it is found that that the amount of by-products formed is reduced by using (m)ethanol. The amount of hydroxide used according to the invention has shown to be sufficient to allow the reaction to work at low temperature and at atmospheric pressure.

In an embodiment, step i) of the method is carried out at a temperature between 10 and 60° C., preferably between 20 and 50° C.

In an embodiment, step ii) of the method is carried out at a pressure of between 0.9 and 1.1 bar (being between 90 and 110 kPa) , such as at ambient pressure.

In an embodiment, the molar ratio between iso-valeraldehyde and sodium hydroxide is between 1:0.1 and 1:0.3, such as an upper limit of 1:0.28.

In an embodiment, the aqueous hydroxide solution has a strength of at least 15% w/v, or at least 20% w/v, such as at least 25% w/v. In an embodiment, the hydroxide base aqueous solution has a strength of at most 50% w/v, such as at most 45% w/v, or at most 40% w/v.

In an embodiment, the molar ratio between iso-valeraldehyde and (m)ethanol hydroxide is between 1.0:0.7 and 1.0:1.0, such as between 1.0:0.8 and 1.0:0.9.

In an embodiment, the molar ratio between (m)ethanol and the hydroxide is between 4.0:1.0 and 8.0:1.0, such as between 5.0:1.0 and 7.0:1:0, there may be approx. 6 times as much mole of (m)ethanol as hydroxide.

In an embodiment, the aqueous solution of a hydroxide base is added gradually, for example dropwise.

In an embodiment, aqueous solution of a hydroxide base is added over a period of between 20 and 60 minutes, such as between 30 and 40 minutes.

The addition of hydroxide will lead to a heat increase (exothermic reaction). In an embodiment, the temperature of the reaction mixture is kept at a temperature of maximally 45° C.

After addition of the hydroxide, the reaction mixture is allowed to react for a period of between 10 and 50 minutes, such as between 20 and 40 minutes, e.g. 30 minutes; preferably at a temperature of between 45 and 65° C., such as between 50 and 55° C.

In an embodiment, the reaction mixture is allowed to cool after reacting to room temperature and phase separation is allowed by stopping mixing, preferably for a period of between 15 and 30 minutes.

In an embodiment, the product is obtained in the form of an oil. The product is present as an organic layer above the aqueous alkali layer and may be removed therefrom. The organic layer may be washed with water to obtain a crude product. Said crude product may be direction used in the following step or may be purified if desired by known purification method. The product is obtained in a yield of approx. 95% and in a purity of above 94%.

Second Step, Step ii)—Reduction

In an embodiment, the reducing system used in step ii) is a nickel aluminium alloy with an inorganic base or a Pd/C (palladium-carbon) catalyst with hydrogen gas.

The use of a nickel aluminium alloy with an inorganic base is preferred since that provides more control over the reaction, leading to less formation of by-products. With this method hydrogen is generated in situ. Moreover, this method is somewhat more mild and safe, which is especially important on plant scale. The experimental part below will show the effect of using nickel aluminium alloy versus palladium carbon. In an embodiment, step ii) will be carried out in an aqueous alkaline solution. An aqueous solution can be used for the reduction reactions therewith reducing the need of organic solvents such as isopropanol and tetrahydrofuran.

In an embodiment, step ii) of the method is carried out at a temperature between 10 and 40° C., for example at least 15° C. or at least 20 or at most 35° C. or at most 30° C. The temperature may be maintained during the addition of the alloy by cooling with e.g. ice water.

In an embodiment, step ii) of the method is carried out at a pressure of between 0.9 (or 1) bar and 3 bar (being between 90 (or 100) bar and 300 kPa) , such as at ambient pressure.

In an embodiment, the nickel-aluminium alloy is added over a period of time of preferably between 1 to 10 hours, such as between 3 and 5 hours.

In an embodiment, the nickel-aluminium alloy is added in the form of a solid, preferably a powder.

In an embodiment, the reaction time after the addition of the alloy is complete is between 4 and 6 hours. The total reaction time during step ii) is preferably between 5 and 7 hours, such as between 5 and 6 hours.

In an embodiment, the molar ratio between the compound according to Formula B and the inorganic base during step ii) is between 1.0:2.0 and 1.0:20.0, preferably between 1.0:3.0 and 1.0:10.0, more preferably between 1.0:4.0 and 1.0:7.0.

In an embodiment, the molar ratio between the compound according to Formula B and the alloy during step ii) is between 1.0:1.0 and 1.0:5.0, preferably between 1.0:1.5 and 1.0:3.0, more preferably between 1.0:1.75 and 1.0:2.25. In this embodiment, at least a stoichiometric amount of alloy is used or an excess of alloy.

In another embodiment, the molar ratio between the compound according to Formula B and the alloy during step ii) is between 20.0 to 1.0 and 5.0 to 1.0, preferably between 20.0 and 1.0 and 6.6 to 1.0, such as 10.0 to 1.0. In this embodiment, between 5 and 20 molar %, such as between 5 and 15 molar %, for example 10 molar % of the alloy is used and in this embodiment hydrogen gas is added to the reaction mixture (e.g. by bubbling) allowing the reaction to go to completion. Without wishing to be bound to a particular theory, the inventors believes that by the reaction of the hydroxide with the nickel aluminium alloy will lead to aluminium salts and the in situ generation of hydrogen that will drive the reaction. In this embodiment, the reaction is started by the alloy acting as a catalyst and the reaction is driven to completion by the addition of additional hydrogen, e.g. by bubbling hydrogen gas through the reaction mixture. This specific embodiment reduces the amount of solid aluminium salt that is added when a stoichiometric or excess of alloy is used.

In an embodiment, as nickel-aluminium alloy was used an alloy comprising between 30 and 50 wt. % of nickel and between 50 and 70 wt. % of aluminium, preferably an alloy comprising 50 wt. % Ni and 50 wt. % Al or 30 wt. % Ni and 70 wt. % Al.

In an embodiment, the alloy is added in at least two, preferably at least three portions; said portions preferably be approximately equal portions. In an embodiment said alloy is added gradually over a period of between 30 and 60 minutes, such as between 40 and 40 minutes, for example 45 minutes. In case more than one portion is added, each portions is added gradually over a period of between 30 and 60 minutes, such as between 40 and 40 minutes, for example 45 minutes. In case more than one portion is added, there is an additional waiting/mixing time between the addition of each portion, being a period of between 30 and 60 minutes, such as between 40 and 40 minutes, for example 45 minutes.

In an embodiment, the product is obtained in the form of an oil.

In an embodiment, said inorganic base in said aqueous solution (forming an aqueous basic solution) is a an alkali hydroxide, preferably sodium hydroxide or potassium hydroxide.

In an embodiment, said aqueous alkaline solution is a solution of sodium hydroxide and/or potassium hydroxide in water.

In an embodiment, first an aqueous alkaline solution is prepared to which is added the (crude) product of Formula B obtained in step i).

In an embodiment, the nickel aluminium alloy is separated as a solid from the liquid reaction mixture obtained after step ii), e.g. by filtration. The retentate (filter cake) may be washed with water. The filtrate comprises both the aqueous solution of an inorganic base as well as the organic product, which can be allowed to separate into two phases. The aqueous alkaline layer may be separated from the organic product layer. The aqueous alkaline layer may be extracted with an extractant, e.g. dichloromethane, to extract further product. Said extractant may be removed by distillation.

In an embodiment, the product is obtained in the form of an oil. The product may be obtained in an amount of 97% and with a purity of approximately 88%. The crude product may be used directly in the following step of may be purified by known methods.

Third Step, Step iii)—Formylation and Reduction

In an embodiment, the inorganic base used in step iii) is selected from the group consisting of a hydroxide base, preferably sodium hydroxide (NaOH) or potassium hydroxide (KOH), or a carbonate base, preferably potassium carbonate ($KCO_3$), and one or more combinations thereof.

In case a hydroxide base is used, it is preferably used as an aqueous solution having a strength of at least 15% w/v, or at least 20% w/v, such as at least 25% w/v. In an embodiment, the hydroxide base aqueous solution has a strength of at most 50% w/v, such as at most 45% w/v, or at most 40% w/v.

In an embodiment, the inorganic base is added gradually to the compound according for Formula C, preferably over a period of between 40 and 80 minutes, such as 1 hour (60 minutes).

The addition of hydroxide will lead to a heat increase (exothermic reaction). In an embodiment, the temperature of the reaction mixture is kept at a temperature of maximally 45° C., or maximally 40° C.

In an embodiment, step iii) of the method is carried out at a temperature between 10 and 40° C., preferably between 20 and 30° C., such as at room temperature.

In an embodiment, step ii) of the method is carried out at a pressure of between 0.9 and 1.1 bar (being between 90 and 110 kPa) , such as at ambient pressure.

In an embodiment, step iii) of the method is carried out for a duration of between 30 and 90 minutes, preferably between 50 and 70 minutes, such as 60 minutes.

In an embodiment, a solvent may be present. In an embodiment, the solvent is selected from the group consisting of methanol or ethanol or a mixture/combination thereof. In an embodiment, formaldehyde is used as a solution in water, such as 36-38 solution that is commercially available.

In an embodiment, the molar ratio between the compound according to Formula C and the inorganic base during step iii) is between 1.0:1.0 and 1.0:3.0, preferably between 1.0:1.4 and 1.0:1.8, such as 1.0:1.6.

In an embodiment, the molar ratio between the compound according to Formula C and formaldehyde in step iii) is between 1.0:2.0 and 1.0:5.0, preferably between 1.0:2.5 and 1.0:3.5, such as 1.0:3.0.

In an embodiment, after the addition of the base is completed, the reaction mixture is stirred at a temperature of between 40 and 60° C., such as between 45 and 50° C. for a period of between 30 and 60 minutes, such as between 40 and 50 minutes, e.g. 45 minutes.

In an embodiment, the reaction mixture is then cooled to room temperature and allowed to settle into phases for a period of between 10 and 50 minutes, such as 30 minutes. The reaction mixture comprises both the aqueous solution of an inorganic base as well as the organic product, which can be allowed to separate into two phases. The aqueous alkaline layer may be separated from the organic product layer. The aqueous alkaline layer may be extracted with an extractant, e.g. dichloromethane, to extract further product. Said extractant may be removed by distillation. The conversion rate of this step may be 100%. The product may be purified prior to the next step, for example by (vacuum) distillation.

Fourth Step, Step iv)—Methylation

In an embodiment, as the methylation agent used in step iv) is dimethyl sulphate or methyl halide, preferably methyl iodide.

In an embodiment, in step iv) the base is selected from the group consisting of hydride base, such as sodium hydride (NaH), a alkoxide base, such as potassium tert-butoxide, or an hydroxide base, such as sodium hydroxide or potassium hydroxide.

In an embodiment, the methylation agent used in step iv) is dimethyl sulphate, viz. $(CH_3O)_2S(=O)_2$ or a methyl halide, viz. $CH_3X$, wherein X is a halide selected from the group of F, CI, I, and Br, preferably methyl iodide, viz. $CH_3I$.

In an embodiment, in step iv) the base is selected from the group consisting of hydride base, such as sodium hydride (NaH), a alkoxide base, such as potassium tert-butoxide, or an hydroxide base, such as sodium hydroxide or potassium hydroxide.

In an embodiment, as the hydroxide base an aqueous hydroxide solution is used, preferably a 40-50% w/v hydroxide solution, more preferable a 45-50% w/v hydroxide solution.

In an embodiment, as the hydride base a 50% sodium hydride solution is used. The use of NaH has the advantage over the use of a alkoxide base is that the conversion rate is higher because it is more active.

In an embodiment, step iv) of the method is carried out at a temperature between 10 and 40° C., preferably between 20 and 30° C., such as at room temperature.

In an embodiment, step ii) of the method is carried out at a pressure of between 0.9 and 1.1 bar (being between 90 and 110 kPa), such as at ambient pressure.

In an embodiment, step iv) of the method is carried out for a duration of between 6 to 12 hours, preferably between 4 and 8 hours.

In an embodiment, a solvent or mixture of solvents may be present. In an embodiment, the solvent may be THF or toluene or a mixture thereof. Preferably a mixture of THF and toluene is used, for example in a ratio of 1:1 to 1:3, such as 1:2.

In an embodiment, the product is obtained in the form of an oil.

In an embodiment, sodium hydride is used in step iv) in an amount of 2-4 mole ratio with respect to the amount of compound according to Formula D (ratio Formula D compound to alkylating agent 1:2 to 1:4).

In an embodiment, said methylation agent is used in step iv) in an amount of 2-4 mole ratio with respect to the amount of compound according to Formula D (ratio Formula D compound to alkylating agent 1:2 to 1:4).

In an embodiment of the present invention, the reaction mixture for step iv) is a biphasic mixture comprising water as one of the phases. In an embodiment, the reaction mixture is a biphasic mixture comprising an aqueous phase (as a first medium) and an organic phase (as a second medium).

The methylation agent may be added in two or more portions. In an embodiment, this addition is carried out at a temperature between 15 and 35° C., such as between 20 and 30° C. In an embodiment, each addition of (a portion of) methylation agent is preferably carried out over a certain period of time, for example dropwise. Said period of time may be for example between 2 and 120 minutes, and it depends on the number of portions that the methylation agent is added in. In an embodiment, wherein said methylation agent is added in two portions, each portion may be added over a period of between 20 and 50 minutes, such as between 30 and 40 minutes. In the embodiment wherein the addition is split into several portions, after each portion of the methylation agent is added, the reaction mixture is stirred for a certain period of time. Said time period may for example be between 10 and 120 minutes, such as between 30 and 40 minutes, prior to the start of the addition of the following portion. In an embodiment, this stirring is carried out at a temperature between 15 and 35° C., such as between 20 and 25° C. After the addition of the methylation agent is completed, the reaction mixture may be further stirred for a certain period of time, such as for example between 2 and 24 hours, preferably between 8 and 12 hours, or overnight.

After the reaction is completed water may be added to the reaction mixture after which the reaction mixture is further stirred for a period of preferably between 5 and 45 minutes, such as between 10 and 20 minutes. The product may then be separated as the organic layer. A product having a purity of >95% may be obtained. The product may be further purified for example by (vacuum) distillation.

EXAMPLES

The present invention is further elucidated based on the Examples below which are illustrative only and not considered limiting to the present invention. All reactions are carried out under nitrogen atmosphere and under ambient pressure. If no information is provided regarding the temperature, the temperature is room temperature. All water used was demineralized water.

Example 1

Step i)

In a 500 ml, ¾-neck round bottom flask fitted with an overhead stirrer and a thermopocket to measure internal reaction temperature and an addition funnel was charged 100 gram (1.16 moles; Molar ratio 1) of iso-valeraldehyde (compound of Formula A). This was followed by the addition of 32 grams of methanol (1 mole; molar ratio 0.86) under stirring. Then 28 millilitres (0.175 moles; 0.15 molar ratio) of a 25% w/v sodium hydroxide solution was gradually (e.g. dropwise) added over a period of 30-40 minutes while the temperature will slowly rise to 45° C. If the temperature reached 45° C. and the addition is not complete, the reaction mixture is cooled. After the addition, the reaction mixture is heated to a temperature of between 50 and 55° C. and maintained at that temperature for a period of 30 minutes. After that the reaction mixture was cooled to room temperature. Then phase separation is allowed to take place for a period of between 15 and 30 minutes without stirring. The lower layer, being the aqueous alkali layer, which is of light yellow colour weighed between 50 and 55 grams and the upper organic product layer (oily) weighed approximately 90 grams. The organic layer was washed with 100 ml of water under stirring and allow to phase separate. The upper organic layer is the crude product of Formula B in the form of an oil in a yield of 85 grams (95%) and with a purity as determined by GC of >94%.

Step ii)

This reaction should be carried out in a hood since hydrogen gas is evolved. In a three liter round bottom flask a NaOH solution—being 156 grams of NaOH (=3.9 moles of NaOH) in 680 ml water (molar ratio of 3)—is prepared and allowed to cool to room temperature. Then 200 grams (1.29 moles; molar ratio of 1) of the crude product of Formula B obtained in step i) was added at once to the alkali solution. Afterwards, a first of three equal lots of 33 grams each of a 50% Ni/Al alloy powder (total amount 99 grams) is added over a period of 45 minutes during which $H_2$ gas evolved. Then the resulting mixture was stirred for another 45 minutes. Afterwards, a second of three equal lots Ni/Al alloy power is added over a period of 45 minutes during which $H_2$ gas evolved. Then the resulting mixture was stirred for another 45 minutes. Afterwards, a third of three equal lots Ni/Al alloy power is added over a period of 45 minutes during which $H_2$ gas evolved. The temperature during each of these additions was kept between 15 and 25° C. using an ice water bath. The reaction mixture was carefully filtered over a Hyflo® filter using a Buchner funnel to remove the Ni/Al-alloy and both the round bottom flask as well as the filter cake were washed with an excess of water. The filtrate was allowed to separate in phases for a period of 1 hour. The lower aqueous layer was removed from the upper organic layer which weighed between 150 and 155 grams and comprises the compound of Formula C. The aqueous layer also comprises some of the product of Formula B which can be recovered by extracting said layer with in total 200 ml of dichloromethane. The dichloromethane layer is combined with the organic layer and distilled without vacuum to obtain between 195 and 197 grams (97%) of crude light yellow oil of compound of Formula C having a purity determined by GC of approximately 88-89%. This compound is directly used in step iii) without additional purification steps.

Step iii)

In a 3 liter 3/4 necked round bottom flask with thermometer pocket, ice cooling bath and overhead stirrer, and addition funnel were added 370 grams (2.13 moles, molar ratio 1) of compound of formula C (obtained in step ii) as well as methanol (417 grams) and a 37% formaldehyde solution in water (522 grams; 6.4 moles; 3.0 molar ratio). Then over a period of 1 hour gradually (dropwise) was added a solution of NaOH (137 grams in 413 ml water; 3.4 moles, molar ratio 1.6), while the temperature was kept below 40° C. (reaction is exothermic). After the addition is complete, the reaction mixture is stirred at a temperature of between 45 and 50° C. for a period of 45 minutes. Then the reaction mixture is cooled to room temperature and allowed to settle into phases for a period of 30 minutes. The oil layer is removed and weighed and the aqueous alkali layer is extracted with dichloromethane (400 ml) which is combined with the organic layer. After distillation on a rotary evaporator product of formula D is obtained in a yield of 404 grams (97% yield) having a purity as determined by GC of 89%; leading hence to a 100% of Formula C to formula D. The product is purified by distillation prior to using it in the following step, 320 grams of product having a purity of >94% is obtained.

Step iv)

In a 3 liter 3/4 necked round bottom flask with thermometer pocket, ice cooling bath and overhead stirrer, and addition funnel was added 300 ml of THF and 600 ml of toluene. The stirring was started and then the compound of Formula D obtained in step iii) (100 grams; 0.53 moles, molar ratio 1.0) was added at room temperature. Then a 50% sodium hydride (72 grams, 1.5 moles, molar ratio 2.8) was gradually added in lots while the temperature is kept below 35° C. After the addition is complete, the reaction is stirred for an additional 30 minutes. Then methyl iodide (184 grams, 1.30 moles, molar ratio 2.45) was added in two equal lots at a temperature of below 30° C. and after each top the mixture was stirred for 30 minutes. After addition, the reaction mixture was stirred for a period of between 10 and 12 hours at room temperature. In order to check the progress of the reaction, small aliquots (2-3 ml) of the reaction mixture were tested for conversion by adding 0.5 ml of methanol and 5 ml of water and then diluting with 5- 10 ml of toluene. The toluene was then checked with GC wherein the monomethyl peak should be absent. Additional methyl iodide may be added if the reaction does not go to completion. When the reaction is complete methanol (25 ml) was added gradually at a temperature of 40° C. Then water (200 ml) was gradually added at a temperature of below 40° C. The resulting mixture is stirred for 15 minutes and separated into layers in a separating funnel. The organic layer was washed with water (100 ml) and then the organic layer evaporated by rotary evaporation to yield 125 grams of crude product having a purity >95%. This final product Formula 1 may be further purified by (vacuum) distillation.

Comparative Example 1: Effect of Methanol in Step i)

In this comparative example no methanol was used.

Step i) was repeated with 1/10 of the amount of all reactants (10 gram of iso-valeraldehyde). The resulting product was obtained in a yield of 95% and a purity of 82%. This clearly shows that methanol has a positive effect on the purity.

Comparative Example 2: Effect of Reduction with Pd/C in Step ii)

To test the effect of the reducing agent, 20 gram of compound of Formula B was hydrogenated with 1.5% Pd/C (0.3 g, 10% form) and 500 ml methanol in autoclave at 20 bar and 80° C. for a period of 5 hours. The composition of the product obtained according to GC was as follows: 75% of the desired compound of Formula C, being 2-isopropyl-5-methyl-2-hexanal, 4% 2-isopropyl-5-methyl-2-hexenol, and 15% 2-isopropyl-5-methylhex-2-enoic acid. Hence the purity was 75% compared to a purity of 88% for the use of the nickel/aluminium alloy.

Comparative Example 3: Effect of Reduction with Pd/C 5% NaOH Without Methanol in Step ii)

To test the effect of the reducing agent, 10 gram of compound of Formula B was hydrogenated with Pd/C (0.1-0.2 g, 5% form) and 5% NaOH solution (40 ml) in an autoclave at 20 bar at room temperature for a period of 2-5 hours. The product obtained according to GC was 93% of the desired compound of Formula C, being 2-isopropyl-5-methyl-2-hexanal, Hence the purity was 93% compared to a purity of 75 for the use of the Pd/C in methanol.

Comparative Example 4: Effect of Reduction with Ni—Al Alloy and 5% NaOH (In-Situ Ggeneration of Active Raney Nickel) in Step ii)

To 5% NaOH solution (100 ml) and 10 gram of compound of Formula B, Ni—Al alloy 50% 1 gm was added and mixture was hydrogenated in autoclave at 20 bar at room temperature for a period of 5-6 hours. The product obtained according to GC was 20 92.5% of the desired compound of Formula C, being 2-isopropyl-5-methyl-2-hexanal.

Comparative example 5: Addition of Sodium Hydride and Iodomethane in Four Lots in Step iv To a mixture of Toluene (60 ml), THF (30 ml) and the compound of Formula D (10 grams) was added at room temperature. Then a 50% sodium hydride (7.2 grams) was gradually added in four equal lots while the temperature was kept below 35° C. After each lot addition stirred for an additional 30 minutes. Then methyl iodide (18.4 grams) was added in four equal lots at a temperature of below 30° C. after each NaOH lot addition and stirring time 30 min. After addition, the reaction mixture was stirred for a period of between 10 and 12 hours at room temperature. Then water (20 ml) was gradually added at a temperature of below 40° C. The resulting mixture was stirred for 15 minutes and separated into layers in a separating funnel. The organic layer was washed with water and then the organic layer evaporated by rotary evaporation to yield 14 grams of crude product having a purity >95%.

The present invention is elucidated by the following claims.

The invention claimed is:

1. A process for the preparation of 2-isopentyl-2-isopropyl-1,3-dimethoxypropane according to Formula 1,

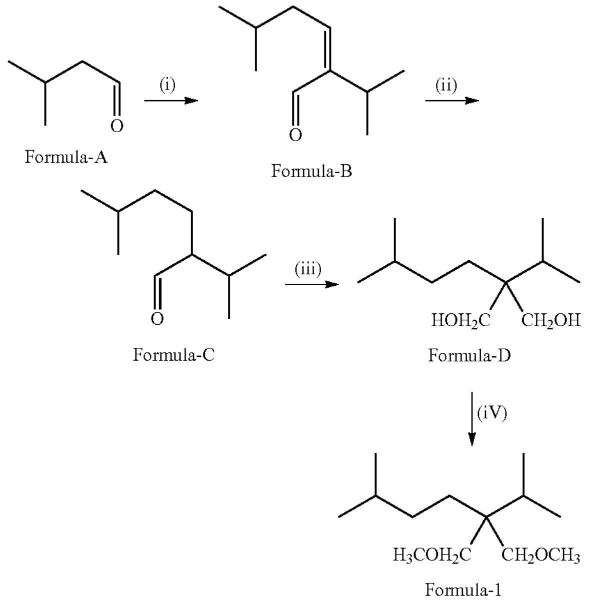

Formula-A, Formula-B, Formula-C, Formula-D, Formula-1 said process comprising the steps of:

step i) contacting iso-valeraldehyde according to Formula A with:

an aqueous solution of a hydroxide base selected from the group consisting of sodium hydroxide (NaOH), potassium hydroxide (KOH) or a combination thereof, said solution having an amount of said hydroxide base of at least 20% w/v, and methanol or ethanol or a combination thereof; to form (2Z)-2-isopropyl-5-methyl-2-hexenal according to Formula B;

step ii) contacting (2Z)-2-isopropyl-5-methyl-2-hexenal according to Formula B with a reducing system to form 2-isopropyl-5-methylhexanal according to Formula C;

step iii) contacting 2-isopropyl-5-methylhexanal according to Formula C with formaldehyde and an inorganic base to form 2-isopentyl-2-isopropylpropane-1,3-diol according to Formula D; and step iv) contacting 2-isopentyl-2-isopropylpropane-1,3-diol according to Formula D with a methylation agent and a base to form 2-isopentyl-2-isopropyl-1,3-dimethoxypropane according to Formula 1;

wherein the molar ratio between the methanol or ethanol or combination thereof and the hydroxide is between 4.0:1.0 and 8.0:1.0.

2. The process according to claim 1, wherein the reducing system used in step ii) is a nickel aluminium alloy with an inorganic base or a Pd/C (palladium-carbon) catalyst with hydrogen gas.

3. The process according to claim 1, wherein the inorganic base used in step iii) is selected from the group consisting of a hydroxide base, or a carbonate base, and one or more combinations thereof.

4. The process according to claim 1, wherein methylation agent used in step iv) is dimethyl sulphate or methyl halide.

5. The process according to claim 1, wherein in step iv) the base is selected from the group consisting of a hydride base, a alkoxide base, or an hydroxide base.

6. A process according to claim 1, wherein step i) comprises:

contacting iso-valeraldehyde according to Formula A with methanol and gradually adding the aqueous solution of a hydroxide base, while the temperature is maintained below 45° C.;

after completion of the addition of the hydroxide heating the reaction mixture to a temperature of between 45 and 60° C. and maintained at that temperature for a period of between 10 and 50 minutes;

separating an aqueous hydroxide phase from an organic product phase;

optionally washing the organic product phase with water;

the organic product phase being (2Z)-2-isopropyl-5-methyl-2-hexenal according to Formula B as an oil.

7. A process according to claim 1, wherein step ii) comprises:

contacting (2Z)-2-isopropyl-5-methyl-2-hexenal according to Formula B with an aqueous solution of hydroxide;

adding Ni/Al alloy in at least three portions, each portion being added gradually over a period of between 30 and 60 minutes and stirring the reaction mixture in between the addition of each portion for a period of between 30 and 60 minutes; while maintaining the temperature between 15 and 25° C.

removing the alloy by filtration; optionally washing the rententate with water;

separating an aqueous hydroxide phase of the filtrate from an organic product phase;

optionally extracting the aqueous hydroxide phase with an organic extractant which extract is combined with the organic product phase;

evaporating the organic product phase to obtain 2-isopropyl-5-methylhexanal according to Formula C.

8. A process according to claim 1, wherein step iii) comprises:

contacting 2-isopropyl-5-methylhexanal according to Formula C with formaldehyde and methanol;

gradually adding an inorganic base, while the temperature is kept below 45° C.;

after completion of the addition of the base heating the reaction mixture to a temperature of between 45 and 60° C. and maintained at that temperature for a period of between 30 and 60 minutes;

separating an aqueous hydroxide phase from an organic product phase;

optionally extracting the aqueous hydroxide phase with an organic extractant which extract is combined with the organic product phase;

evaporating the organic product phase to obtain crude 2-isopentyl-2-isopropylpropane-1,3-diol according to Formula D;

optionally purifying the crude 2-isopentyl-2-isopropylpropane-1,3-diol according to Formula D obtained by distillation.

9. A process according to claim 1, wherein step iv) comprises:

contacting 2-isopentyl-2-isopropylpropane-1,3-diol according to Formula D with one or more solvents;

gradually adding a base;

after completing of the addition allowing the reaction mixture to react for a period of between 10 and 50 minutes;

adding methyl iodide in at least two portions, and stirring the reaction mixture in between the addition of each portion for a period of between 10 and 50 minutes;

after completing of the addition allowing the reaction mixture to react for a period of between 8 and 14 hours;

separating an aqueous hydroxide phase from an organic product phase being crude 2-isopentyl-2-isopropyl-1,3-dimethoxypropane;

optionally washing the crude 2-isopentyl-2-isopropyl-1,3-dimethoxypropane with water to obtain 2-isopentyl-2-isopropyl-1,3-dimethoxypropane as an oil.

* * * * *